(12) United States Patent
Drouin et al.

(10) Patent No.: US 6,869,560 B1
(45) Date of Patent: Mar. 22, 2005

(54) PROCESS FOR MANUFACTURING A FLEXIBLE SLEEVE FOR A PROSTHESIS OR ORTHESIS, PREFORM USED IN THIS PROCESS AND FLEXIBLE SLEEVE THUS OBTAINED

(75) Inventors: Vincent Drouin, Beaume (FR); Olivier Pierron, Brazey en Plaine (FR)

(73) Assignee: Establissements Proteor, Saint Apollinaire (FR)

( * ) Notice: Subject to any disclaimer, the term of this patent is extended or adjusted under 35 U.S.C. 154(b) by 774 days.

(21) Appl. No.: 09/692,956

(22) Filed: Oct. 20, 2000

(30) Foreign Application Priority Data

Oct. 22, 1999 (FR) .......................................... 99 13202

(51) Int. Cl.⁷ .............................................. B29C 43/56
(52) U.S. Cl. ........................ 264/500; 264/571; 264/222
(58) Field of Search ................................ 264/500, 571, 264/222; 425/2

(56) References Cited

U.S. PATENT DOCUMENTS

| | | | |
|---|---|---|---|
| 4,473,421 A | * | 9/1984 | Gustafsson ................. 156/214 |
| 4,704,129 A | | 11/1987 | Massey |
| 5,376,127 A | | 12/1994 | Swanson |
| 5,376,132 A | * | 12/1994 | Caspers ........................ 623/36 |
| 5,658,354 A | * | 8/1997 | Norvell ........................ 623/36 |
| 5,888,216 A | * | 3/1999 | Haberman .................... 623/36 |
| 6,136,039 A | * | 10/2000 | Kristinsson et al. .......... 623/36 |

FOREIGN PATENT DOCUMENTS

| | | |
|---|---|---|
| EP | 0 207 758 A2 | 1/1987 |
| EP | 0 380 345 A1 | 8/1990 |
| EP | 0 631 765 A1 | 1/1995 |
| GB | 2 148 177 A | 5/1985 |

* cited by examiner

*Primary Examiner*—Suzanne E. McDowell
(74) *Attorney, Agent, or Firm*—Scully, Scott, Murphy & Presser

(57) ABSTRACT

A process for manufacturing a flexible sleeve for a prosthesis or orthesis, including selecting sleeve preform (2) which consists of flexible thermoformable material and having approximately conical or cylindrical shape with a closed end of rounded shape the dimensions of which are matched to those of the stump or stump replica to be fitted with the prosthesis or with the orthesis; heating the preform (2) until it softens; slipping the softened preform over the stump or over the stump replica (1); conforming the shape of the softened preform (2) to that of the stump or of its replica (1); leaving the preform (2) to cool on the stump or on the replica; and removing the cooled preform which constitutes the finished sleeve from the stump or the stump replica.

3 Claims, 2 Drawing Sheets

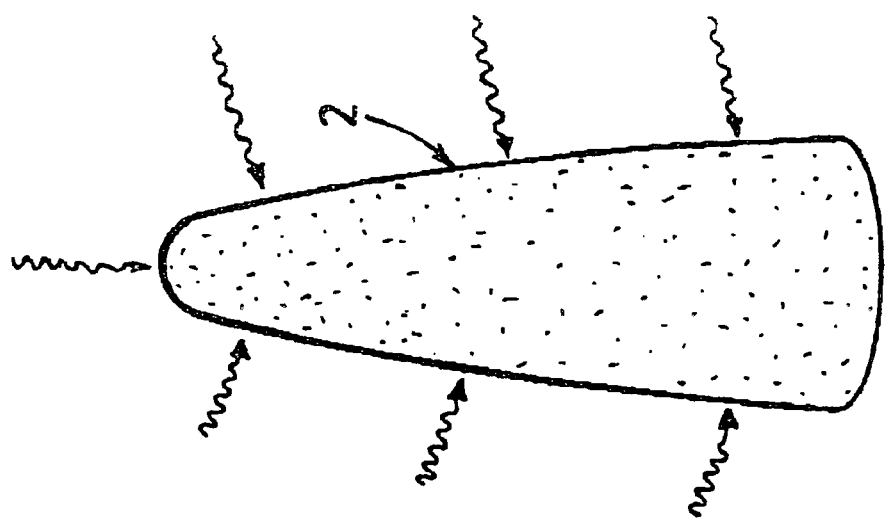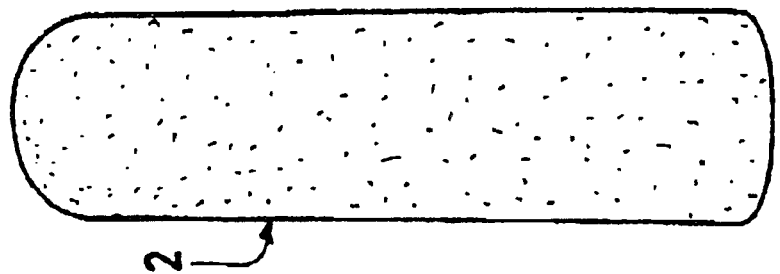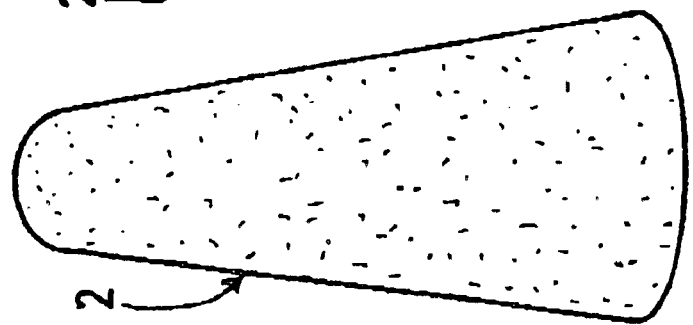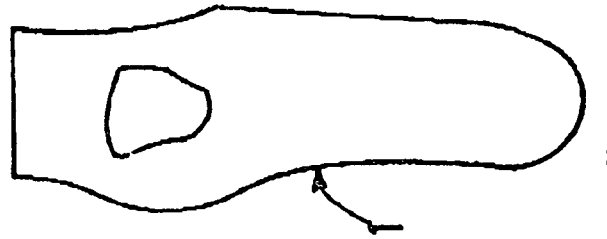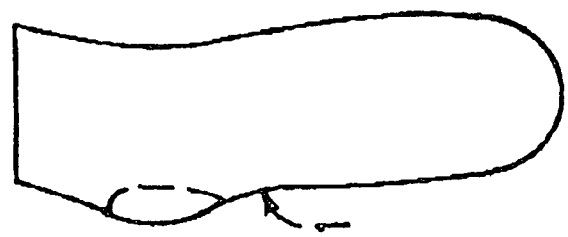

PROCESS FOR MANUFACTURING A FLEXIBLE SLEEVE FOR A PROSTHESIS OR ORTHESIS, PREFORM USED IN THIS PROCESS AND FLEXIBLE SLEEVE THUS OBTAINED

The invention relates to a process for manufacturing a sleeve for a prosthesis or orthesis, to the preform of this sleeve, used in this process, and to the sleeve thus obtained.

PRIOR ART

In certain cases associated with pathology or with amputation, an external prosthesis requires an interface between the stump and its socket. This interface, called a sleeve, allows the stump to be protected from the stresses, such as impacts and frictional forces, that arise when walking, standing or sitting, or even when simply fitting the prosthesis.

Hitherto, the sleeve has been produced from precise measurements of the stump and by means of various materials such as rubber, leather, silicone gel, polyurethane gel, and by applying various processes, such as molding, countermolding, adhesive bonding, injection molding.

However, these techniques require a specific know-how on the one hand, and a relatively long manufacturing time on the other.

BRIEF DESCRIPTION OF THE INVENTION

The Applicant therefore carried out research in order to remedy the drawbacks that have just been mentioned. The Applicant achieved this by using a sleeve preform consisting of a prefabricated hollow element made of a flexible thermoformable material, which makes it possible to omit the current steps of producing a model and of cutting, grinding, adjusting, bonding and drying the latter.

The subject of the present invention is consequently a process for manufacturing a flexible sleeve intended to serve as interface between a prosthesis or an orthesis and a portion of a patient's limb, characterized in that it comprises the following successive steps:

- a sleeve preform (2) [sic] is chosen, which consists of a prefabricated hollow element made of a flexible thermoformable material, of approximately conical or cylindrical shape, having a closed end of rounded shape, the dimensions of which are matched to those of the stump intended to be fitted with the prosthesis or with the orthesis;
- this preform is heated until it softens;
- this softened preform is slipped over the stump or over a replica thereof;
- the shape of the softened preform is matched to that of the stump or of its replica;
- the preform thus shaped is left to cool on the stump or on its replica;
- the flexible cooled preform, which constitutes the desired sleeve, is removed from the stump or from its replica.

The subject of the invention is also the flexible sleeve preform, consisting of a prefabricated hollow element, made of a flexible thermoformable material, of approximately conical or cylindrical shape, having a closed end of rounded shape, which is used in this process.

This preform may, for example, be made of a closed-cell or open-cell foam of polyolefin or of ethylene-vinyl acetate (EVA), or be made of any other thermoformable material that can be used on an industrial scale for such an application. This preform may also consist of a blend of two or more thermoformable materials.

The invention also relates to the flexible sleeve which is obtained by the process defined above and which is intended to be interposed between the patient's stump, covered by this sleeve, and a rigid socket intended to be fitted to the stump, for example the rigid socket described in U.S. Pat. No. 4,704,129.

This flexible sleeve perfectly replicates the patient's stump and, consequently, provides the patient with much greater comfort than that provided by the sleeves of the prior art. In particular, the use of a preform, prefabricated by molding, especially by injection molding, which is matched to the shape of the stump, without having to make use of any adhesive bonding, dispenses with the bonding regions of the sleeves of the prior art, which sleeves proved to be painful for the patient and could even injure him.

Further features and advantages of the invention will emerge from the detailed description which follows, in which reference will be made to the appended schematic drawings.

BRIEF DESCRIPTION OF THE DRAWINGS

FIGS. 1a and 1b show schematically a stump or its replica (a "positive"), seen from the side and from the front;

FIGS. 2a and 2b show schematically two preforms from which the sleeve may be manufactured;

FIG. 3 illustrates the operation of heating a preform placed on the replica of the stump;

DETAILED DESCRIPTION OF THE INVENTION

The invention may be carried out in several ways, depending on whether or not the softening temperature of the material of which the preform is made can be withstood by the patient.

When this temperature is too high, a molding, then a counter molding, of the patient's stump is made, resulting in a positive, corrected or uncorrected, molding of this stump, like the one depicted by reference 1 in FIGS. 1a and 1b.

If the material used has quite a low softening temperature, it is not necessary to make use of a positive, and the entire phase of taking impressions and of grinding the positive is thus advantageously dispensed with.

The next step is to choose a hollow preform 2 of the sleeve, made of a flexible thermoformable material, manufactured by molding, for example of roughly conical shape (FIG. 2a) or roughly cylindrical shape (FIG. 2b), having a closed end of rounded shape, the dimensions of which are matched to those of the patient's stump. The choice of the preform is made by measuring the perimeter of the stump or of the positive at a defined distance from its end and by comparing it with the corresponding dimension of the preform at a corresponding place.

The preform 2 adopted is then heated (FIG. 3), for example in an oven, or using a hot-air gun, or by any other means known in the art, and, when it has softened sufficiently, it is slipped over the stump or over the positive 1 corresponding to the latter.

Figure 4:
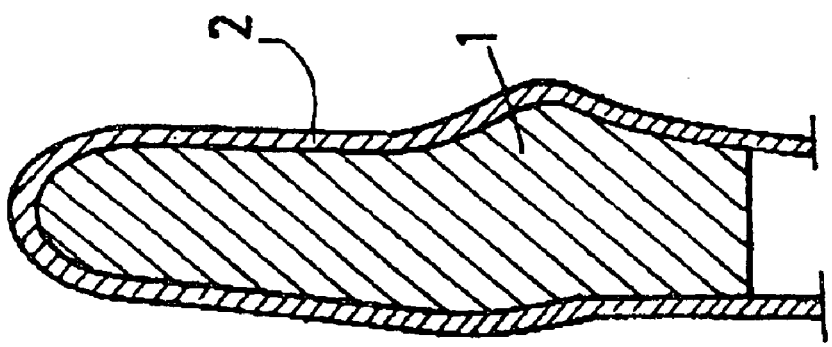
FIG. 4 is a cross-sectional view of the preform placed on the replica of the stump, after shaping it to the contours of this replica.

Because of the softening of the preform 2, it is then possible to make it closely follow the shape of the stump or of the positive 1 (FIG. 4), by exerting pressure on the external surface of the sleeve or exerting a vacuum inside the latter, the preform 2 thus being shaped perfectly to the contours and to the dimensions of the stump or of the positive used.

Figure 6:
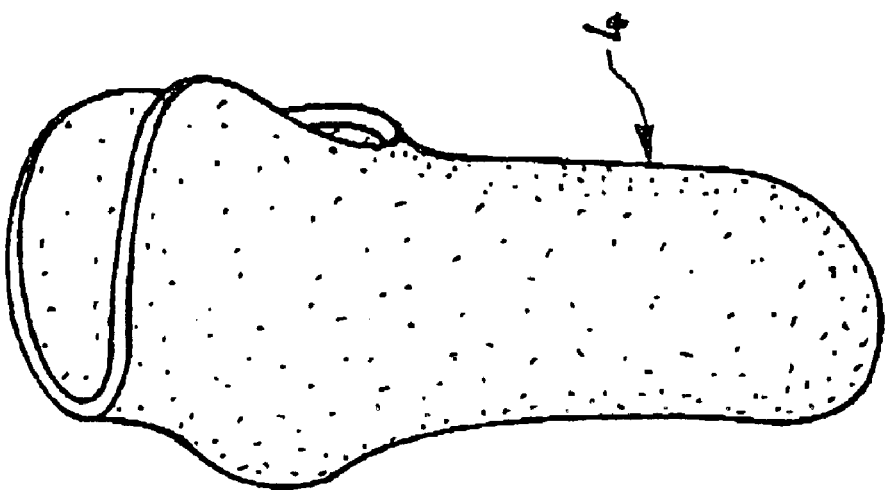
FIG. 6 is a perspective view of the ready-to-use sleeve.
Figure 5:
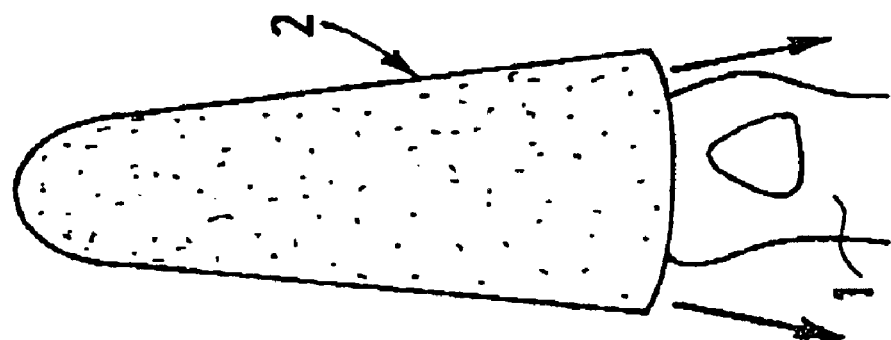
FIG. 5 illustrates the demolding of the cooled sleeve thus produced.

After cooling the preform, it is merely a question of removing it from the stump or from the positive 1 (FIG. 5) in order to obtain a flexible sleeve 4 (FIG. 6), the shape and the dimensions of which correspond exactly to those of the patient's stump. The upper cuts in the sleeve 4 are then produced using a cutting tool and the edges of the sleeve are preferably ground, in order to avoid injuring the patient, over the stump of whom the sleeve may be fitted without any further modification.

The invention therefore provides a particularly simple means, which is easy to employ and is inexpensive, for producing sleeves which faithfully match the shape and the dimensions of the stump of a patient for whom this sleeve is intended.

What is claimed is:

1. A process for manufacturing a flexible sleeve serving as interface between a prosthesis or an orthesis and a stump or stump replica of a limb of a patient, wherein said process comprises the steps of:

selecting a sleeve preform (2) of generally conical or cylindrical shape, which consists of a prefabricated hollow element made of a flexible thermoformable material selected from the materials consisting of a polyolefin foam, an ethylene-vinyl acetate foam by themselves or a blend of said materials with other thermoformable materials;

said sleeve preform having a closed end of rounded shape possessing dimensions, which are matched to those of the stump, or stump replica which is to be fitted with the prosthesis or with the orthesis;

heating said sleeve preform (2) until said preform softens;

slipping said softened sleeve preform (2) over the stump or stump replica (1) thereof;

matching the shape of the softened sleeve preform (2) to that of the stump or of the stump replica (1);

cooling the shaped preform (2) while being arranged on the stump or on the stump replica; and removing the flexible cooled sleeve preform which constitutes the final sleeve (4) from the stump or from the stump replica.

2. A process according to claim 1, wherein the softened flexible preform (2) is conformed to the shape of the stump or of the stump replica (1) thereof by exerting an external pressure against said sleeve.

3. A process according to claim 1, wherein the softened flexible preform (2) is conformed to the shape of the stump or of the stump replica (1) thereof by imparting a vacuum to the interior of said sleeve preform.

* * * * *